(12) United States Patent
Fowler et al.

(10) Patent No.: US 6,635,031 B2
(45) Date of Patent: Oct. 21, 2003

(54) SURGICAL SYSTEM PUMP AND METHOD THEREFOR

(75) Inventors: Reginald H. Fowler, Meridian, TX (US); Garrett L. Barker, Meridian, TX (US); C. Kenneth French, Cranfills, TX (US); Daniel A. Palmer, Hamilton, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 17 days.

(21) Appl. No.: 10/300,214

(22) Filed: Nov. 20, 2002

(65) Prior Publication Data

US 2003/0069540 A1 Apr. 10, 2003

Related U.S. Application Data

(63) Continuation of application No. 09/564,014, filed on May 3, 2000.

(51) Int. Cl.[7] ............................................. A61M 37/00
(52) U.S. Cl. .................... 604/131; 604/890.1; 604/151; 604/257; 604/31
(58) Field of Search ............................ 417/1; 604/131, 604/890.1, 891.1, 892.1, 151, 152, 153, 257, 27, 28, 30, 31, 35

(56) References Cited

U.S. PATENT DOCUMENTS

| | | | |
|---|---|---|---|
| 5,188,591 A | 2/1993 | Dorsey, III | 604/33 |
| 5,391,145 A | 2/1995 | Dorsey, III | 604/33 |
| 5,423,746 A | 6/1995 | Burkett et al. | 604/65 |
| 5,484,402 A | 1/1996 | Saravia et al. | 604/35 |
| 5,522,796 A | 6/1996 | Dorsey, III | 604/118 |
| 5,573,504 A | 11/1996 | Dorsey, III | 604/35 |
| 5,718,668 A | 2/1998 | Barnett et al. | 601/155 |
| 5,791,880 A | 8/1998 | Wilson | 417/14 |
| 5,807,313 A | 9/1998 | Delk et al. | 604/35 |
| 5,840,068 A | 11/1998 | Cartledge | 604/131 |
| 5,904,666 A | 5/1999 | DeDecker et al. | 604/65 |
| 5,904,668 A | 5/1999 | Hyman et al. | 604/131 |
| 5,984,894 A | 11/1999 | Poulsen et al. | 604/151 |
| 5,993,420 A | 11/1999 | Hyman et al. | 604/131 |
| 6,106,494 A | 8/2000 | Saravia et al. | 604/35 |
| 6,162,194 A | 12/2000 | Shipp | 604/151 |
| 6,176,847 B1 | 1/2001 | Humphreys, Jr. et al. | 604/246 |
| 6,196,992 B1 | 3/2001 | Keilman et al. | 604/67 |
| 6,203,528 B1 | 3/2001 | Deckert et al. | 604/131 |
| 6,328,712 B1 | 12/2001 | Cartledge | 604/113 |

*Primary Examiner*—Teresa Walberg
*Assistant Examiner*—Fadi H. Dahbour
(74) *Attorney, Agent, or Firm*—Robert C. Kain, Jr.; Fleit Kain

(57) ABSTRACT

The automatically controlled pump includes a battery-powered motor with a housing, a pump in a housing with input and output ports. A switch turns ON and OFF the motor due to fluid pressure at the output. Sometimes, the pump housing is below the motor housing and below the battery housing. The input port is beneath the impeller and the output port. A version also includes a manual ON and OFF switch actuated by an operator and a check valve limiting upstream flow of the pressurized fluid. The fluid pressure sensitive switch is mounted downstream of the check valve. An irrigation surgical kit includes the automatically controlled pump, a spike for a fluid source bag, fluid lines and an operator controlled valve unit disposed at or near the surgical site. The method monitors fluid pressure at or near the pump's output and turns ON and OFF the motor.

18 Claims, 4 Drawing Sheets

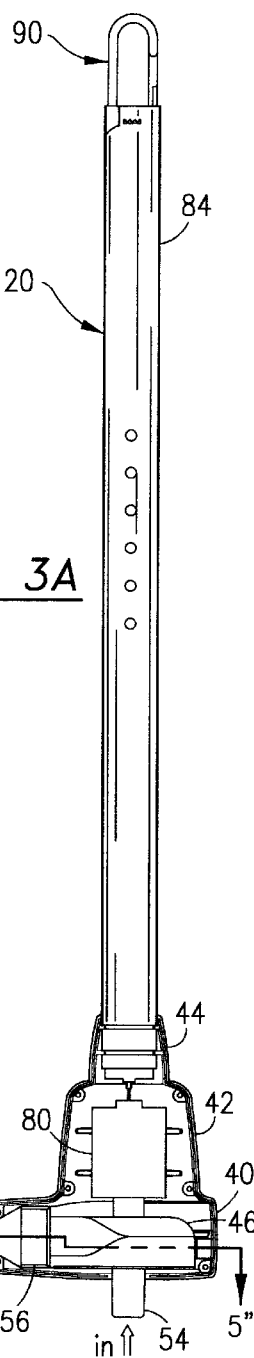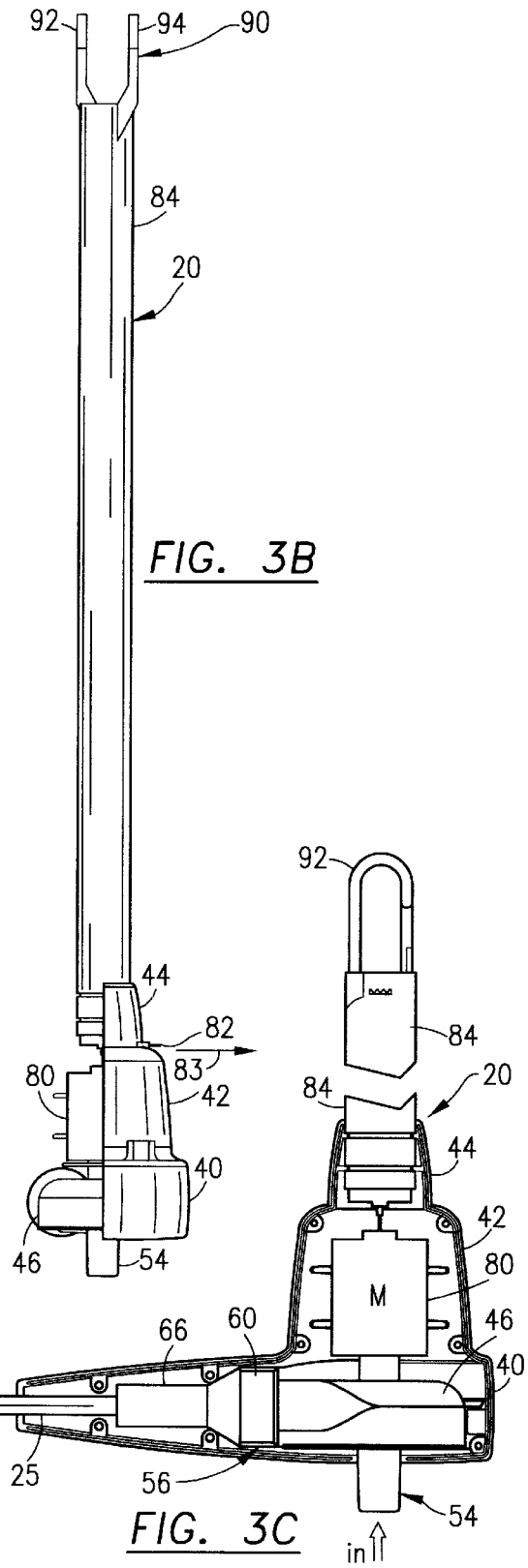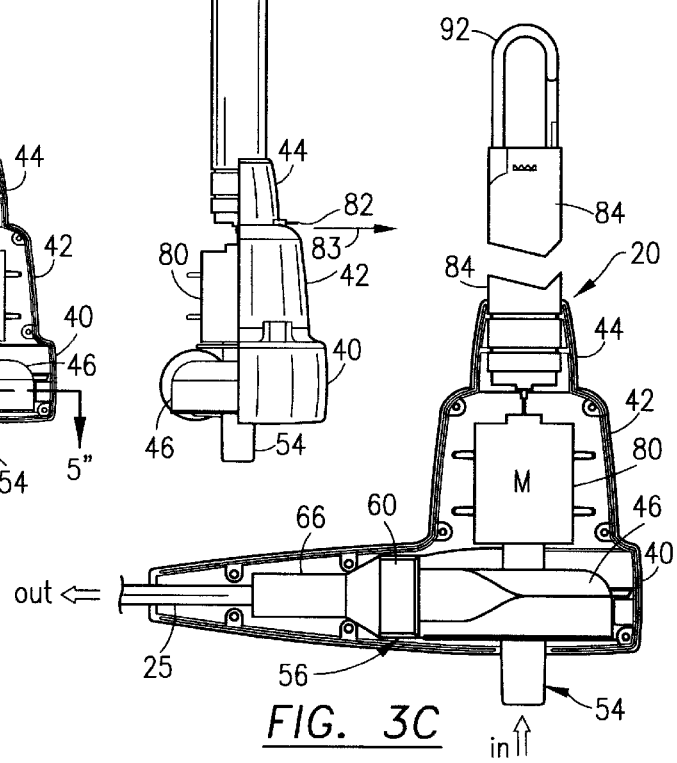

SURGICAL SYSTEM PUMP AND METHOD THEREFOR

This is a continuation U.S. patent application Ser. No. 09/564,014, filed May 3, 2000.

The present invention relates to an automatic pump system, typically used to supply pressurized irrigation fluid to a surgical site, and a method therefor.

BACKGROUND OF THE INVENTION

In many instances, a physician and other health professional (sometimes referred to herein as an "operator") utilizes irrigation fluid to cleanse and wash a wound at a surgical site. This irrigation fluid (sometimes generally referred to herein as "fluid") is specially prepared for this medical procedure. In many instances, the fluid is retained at a fluid source which, in most situations, is a sterile bag containing irrigation fluid. Sterilized water is typically used in such medical procedures.

The physician or operator controls the flow of irrigation fluid by a simple valve control or valve unit at or near the surgical site. In some instances, this valve unit includes a second valve which controls suction such that the physician or operator can remove irrigation fluid, debris and other bodily fluids from the surgical site by activating the second valve in the valving unit and drawing the spent irrigation fluid from the surgical site with a vacuum or suction line.

U.S. Pat. No. 5,807,313 to Delk et al. discloses a battery powered surgical irrigator system. In this prior art system, an electrical switch is mounted immediately adjacent the valve unit which controls the flow of irrigation fluid. The valve unit includes an irrigation fluid valve and a suction valve. In order to turn ON and OFF the pump supplying pressurized irrigation fluid, the operator depresses an electrical control switch mounted on the valving unit. The pump is located beneath the bag holding the supply of irrigation fluid.

U.S. Pat. No. 5,484,402 to Saravia et al. discloses a surgical suction irrigator. In this system, the irrigation and suction valve control also enclose and include an electrical switch. The pump which supplies pressurized fluid to the valve unit, is mounted beneath the bag of irrigation fluid.

U.S. Pat. No. 5,718,668 to Arnett et al. discloses an irrigation hand piece with a built in pulsating pump. This system utilizes a hand piece which includes a pump, a battery power supply for the pulsating pump motor and an electrical switch all mounted in the suction and irrigation valve unit.

OBJECTS OF THE INVENTION

It is an object of the present invention to provide an automatic pump system which eliminates the need for a manual or operator actuated switch to turn ON and OFF the pump supplying a pressurized supply of surgical fluid to the surgical site.

It is another object of the present invention to provide an automatically controlled pump wherein the pump control monitors pressure on or at the output of the pump thereby ensuring a pressurized supply of surgical fluid to the surgical field via a remotely disposed valving unit.

It is a further object of the present invention to provide a pump system which hangs from the stand wherein the stand further carries the bag of surgical fluid supply.

It is an additional object of the present invention to provide an automatic pump system wherein the fluid input to the pump is beneath the pump's output. In a preferred embodiment, the pump housing is disposed beneath a motor and a motor housing which, in turn, is disposed beneath an elongated housing within which is mounted at least one and, preferably, a plurality of batteries.

It is an additional object of the present invention to provide a disposable automatic pump system for a surgical suite.

It is another object of the present invention to provide an irrigation surgical kit which includes a spike, to be forcibly inserted into a fluid source bag, first and second fluid or hydraulic lines, an automatically controlled pump and an irrigation valve control unit.

It is another object of the present invention to provide a method for automatically controlling an irrigation supply pump wherein fluid pressure is monitored at or near the pump output and, based upon fluid pressure above or below a predetermined value, the battery power supplied to the motor driving the pump is turned ON and OFF.

SUMMARY OF THE INVENTION

The automatically controlled pump supplies pressurized irrigation fluid via an output line to a surgical site. The pump is coupled to a fluid source via an input line. The pump system includes a motor, a motor housing, a pump disposed within a pump housing and fluid input and fluid output ports defined by the pump housing. The pump has a rotatably disposed impeller coupled to the motor. The input and output lines are respectively coupled to the fluid input and output ports. The motor is powered by at least one battery and preferably a plurality of batteries. A switch turns ON and OFF the motor and is controlled by fluid pressure at or near the fluid output port. In a further enhancement, the pump housing is attached below the motor housing and the motor housing is attached below a battery housing which contains a plurality of batteries. The pump's input port is disposed beneath the pump's impeller and the pump's output port. The pump's output port is disposed laterally with respect to the impeller. A version of the system also includes a manual ON and OFF switch actuated by an operator and a check valve limiting upstream flow of the pressurized fluid. The fluid pressure sensitive switch is mounted downstream of the check valve. The irrigation surgical kit includes the automatically controlled pump, a spike adapted to be forcibly inserted into the fluid source bag, first and second fluid carrying lines and an operator controlled valve unit disposed at or near the surgical site. The method of automatically controlling a pump includes providing a battery powered motor mechanically coupled to the pump, the step of monitoring fluid pressure at or near the pump's output and turning ON and OFF the motor based upon fluid pressure above or below a predetermined value in the output line coupled to the pump's output port.

BRIEF DESCRIPTION OF THE DRAWINGS

Further objects and advantages of the present invention can be found in the detailed description of the preferred embodiments when taken in conjunction with the accompanying drawings in which:

FIGS. 3A and 3B diagrammatically illustrate partial, cross-sectional views of the automatic pump system;

FIG. 3C diagrammatically illustrates a detailed, cross-sectional view of the pump system;

DETAILED DESCRIPTION OF THE PREFERRED EMBODIMENTS

The present invention relates to an automatically controlled pump or pump system for supplying pressurized fluid to a surgical site and a method therefor and an irrigation surgical kit.

Figure 1:
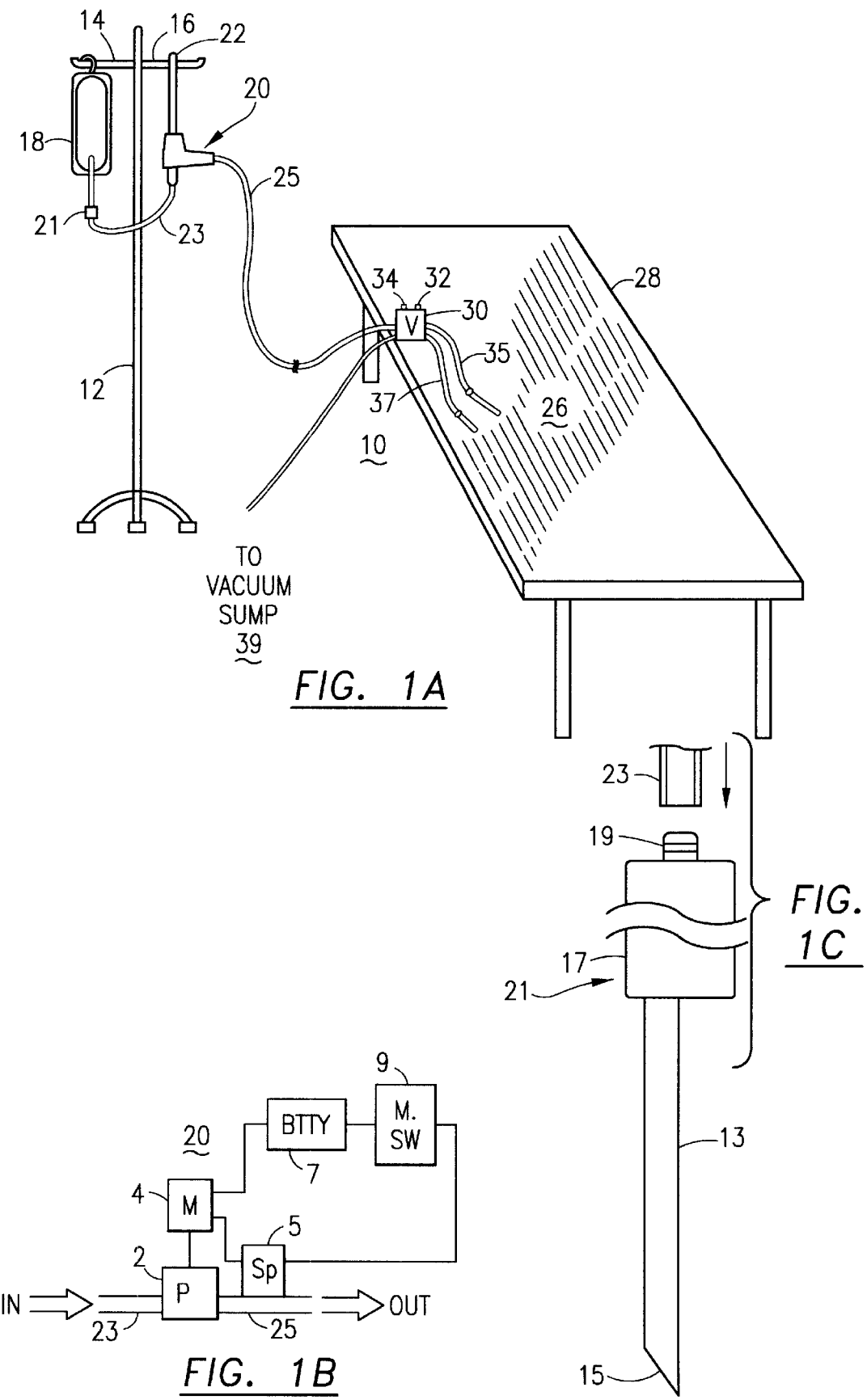
FIG. 1A diagrammatically illustrates certain aspects of a surgical suite including the source of surgical fluid (irrigation fluid), an automatic pump system provided in accordance with the principles of the present invention, input and output lines, and an operator controlled irrigation and suction unit (collectively, an irrigation surgical kit except for the source of fluid)
FIG. 1B diagrammatically illustrates a block diagram showing fluid control and electrical components of the automatic pump system in accordance with the principles of the present invention.
FIG. 1C diagrammatically illustrates the spike utilized to provide fluid access to the source of surgical fluid (the bag)

FIG. 1A diagrammatically illustrates a surgical suite, or the relevant portions thereof, in suite 10. Suite 10 includes a stand 12 which has hanger bars 14, 16. A source of irrigation fluid is found in bag 18 hung on hanger bar 14. Automatic pump 20 is hung via terminal end 22 on hanger bar 16. In the preferred embodiment, automatic pump system 20 is disposable. Pump system 20 is supplied with fluid via input line 23. Pump system 20 supplies pressurized fluid via output line 25 to the surgical site generally located in area 26 on table 28. An operator controls the flow of fluid, typically irrigation fluid, via valve system 30. In many situations, valve system 30 includes an irrigation line control valve 32 and a suction line control valve 34 and respective suction and irrigation lines 35, 37 extending from valve unit 30 to surgical site 26. Suction line 37, after passing through valve unit 30, is coupled to a vacuum source and sump 39.

There are many different types of valve control units that may be used in connection with the automatic pump system and kit in accordance with the principles of the present invention. For example, U.S. Pat. No. 5,522,796 to Dorsey; U.S. Pat. No. 5,188,591 to Dorsey; U.S. Pat. No. 5,391,145 to Dorsey; U.S. Pat. No. 5,391,145 to Dorsey and U.S. Pat. No. 5,573,504 to Dorsey disclose operator controlled valving systems. Valve system or unit 30 is sold as part of an irrigation surgical kit which additionally includes output line 25 (typically about 12 feet in length), automatic pump 20, input line 23 (typically 12 inches in length) and spike 21. Pump 20 is preferably disposable. The batteries (size AA) are removed by "cracking open" the battery housing. Although the present invention is primarily directed toward pump system 20, in some instances, automatic pump system 20 is incorporated into a surgical kit which includes the aforementioned items. Various valve systems 30 may be utilized in connection with automatically controlled pump 20.

FIG. 1B diagrammatically shows the fluid control and electrical system for the present invention. Pump P2 is mechanically driven by motor M4. Pump P is supplied with a source of fluid via input line 23. Pump P generates pressurized fluid (when motor M is turned ON) on output line 25. As used herein, the term "pressurized fluid" or the phrase "a pressurized supply of surgical fluid" refers to fluid under a pressure greater than the fluid pressure in input line 23. Typically the pressure in output line 25, when pump P is turned ON, is approximately 5 psi.

One of the key features of the present invention is the use of a fluid pressure sensitive switch Sp 5 which is mounted or disposed at or near the output port of pump P. Pump system 20 automatically detects when the pressure in output line 25 falls below a predetermined value (approximately 5 psi). Upon detecting that low pressure, switch Sp closes the electrical circuit between battery 7 and motor M. In addition, the operator is provided with a manual ON switch 9. In most instances, after pump 20 is mounted on hanger bar 16 or is otherwise placed in use, the operator closes manual switch 9 and the pump operates automatically. Sometimes, the fluid or hydraulic system must be primed or filled with fluid before the pump operates automatically. When pressure in output line 25 falls below a predetermined value (or a range of values), switch Sp closes thereby supplying electrical power to motor M which drives pump P which further supplies pressurized fluid to output line 25. When the correct pressure is achieved in line 25, the switch opens, power is removed from the motor and the pump stops.

Referring to FIG. 1A, the basic diagram of a surgical suite, pressurized fluid (typically irrigation fluid) is supplied via output line 25 to the operator controlled valving unit 30. Valving unit 30 is typically disposed at a remote location away from stand 12 that holds fluid supply 18 and pump system 20. By providing an automatic ON and OFF control and generally uniform pressure in output line 25, the physician or operator, by closing irrigation valve (either valve 32 or valve 34) in valving unit 30, can deliver a controlled constant flow or a variable flow (dependent upon the position of valve 32) of irrigation fluid to surgical site 26.

The present system avoids the use of an additional electrical line mechanically coupled and extending along the length of fluid output line 25 to an electrical motor in pump system 20. See U.S. Pat. No. 5,807,313. Further, the present invention avoids the necessity of an operator controlled ON/OFF switch in addition to irrigation and suction valve controls 32, 34 at valving unit 30. The reduction of operator controls enhances the operator's ability to more efficiently clean and treat the wound or other item at surgical site 26.

FIG. 1C diagrammatically shows spike 21 which includes a rigid tube 13, a sharp end 15, a hand piece 17, and a hose coupling unit 19.

Figure 2:
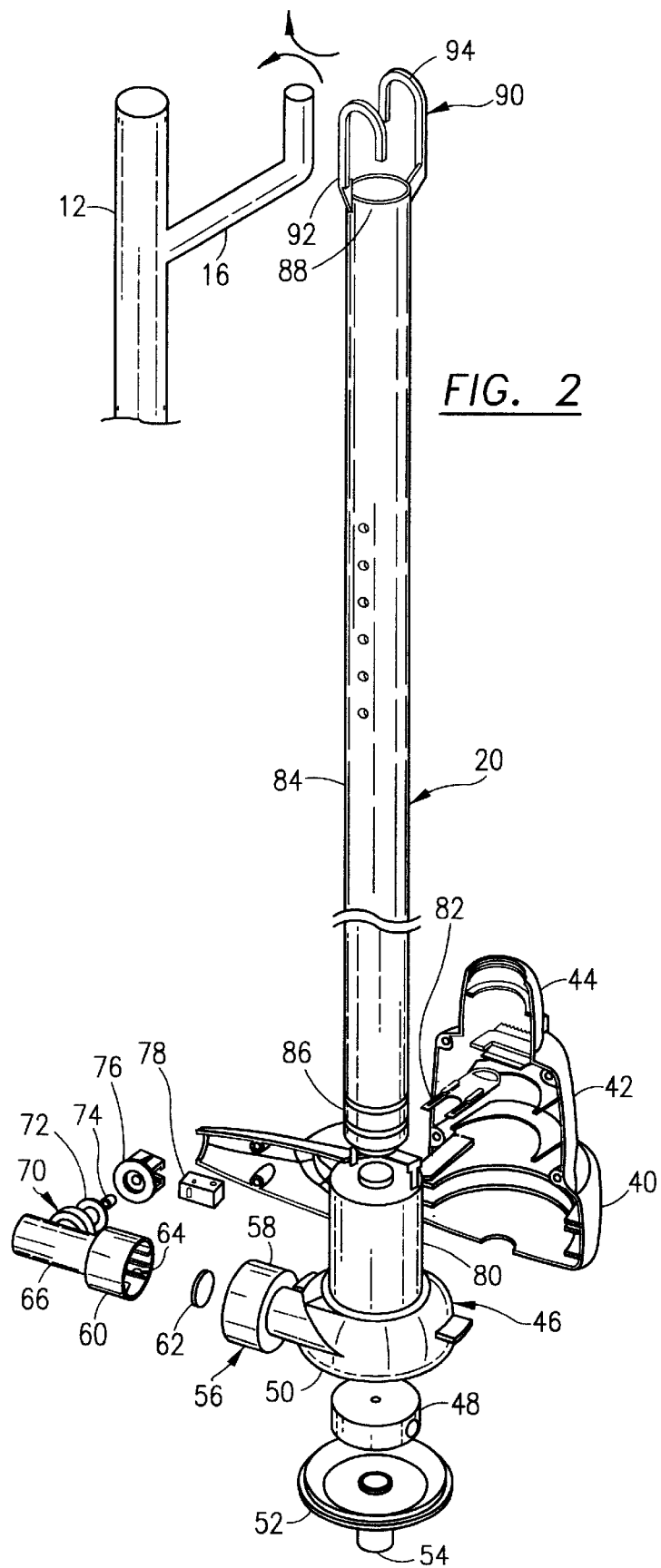
FIG. 2 diagrammatically illustrates a partial, exploded, perspective view of the automatic pump system and the hanger mechanism to mount the pump system on the medical stand.

FIG. 2 diagrammatically shows automatic pump system 20 as a partial, exploded view. Pump system 20 includes exterior pump housing 40, motor housing 42 and collar 44. Exterior pump housing 40 contains interior pump housing 46. A chamber inside interior pump housing 46 is established to rotatably contain pump impeller 48. Interior pump housing 46 includes upper housing 50 and a lower housing 52. In one embodiment, lower housing 52 is threadibly attached (with a fluid and pressure seal) to upper housing 50. Impeller 48 rotates in a chamber (identified later) established between upper and lower housings 50, 52. Alternatively, the lower housing may be solvent bonded or snap fit onto the upper housing.

Pump housing 46 defines a fluid input port 54 and a fluid output port 56. Fluid output port 56 includes proximal body 58 and distal body 60. A check valve having a check valve disc 62 is mounted in interior space 64 defined by proximal and distal output port bodies 58, 60. Pump output port 56 also includes nozzle body 66. A fluid pressure sensitive switch 70 is mounted thereon. Fluid pressure sensitive switch 70 is mounted downstream of the check valve and particularly check valve disc 62. However, pressure sensitive switch 70 is mounted at or near the pump's output port 56.

Pressure sensitive switch 70 includes a diaphragm 72 which limits fluid flow from the interior of nozzle 66 to the electrical components within switch 70 and the mechanical actuator member 74. Actuator member 74 moves within switch body 76. Switch body 76 also includes a fluid sealing system to limit fluid flow from the interior of nozzle body 66. Pressure sensitive switch 70 also includes a small electrical switch 78 which is sometimes referred to as a "micro switch." Micro switch 78 is electrically connected to motor 80.

Motor 80 is mounted within motor housing 42. The drive shaft of motor 80 is mechanically coupled to pump impeller 48. A manual ON/OFF switch 82 enables the operator to pull slide switch 82 outward or outbound thereby closing the electrical contact between the batteries in battery housing 84 and the balance of the electrical circuit which includes the motor. Battery housing 84 has a proximal end 86 attached to collar 44 and to the upper portion of motor housing 42. Housing 84 also has a distal, terminal end 88. A hanger system 90 is defined at the terminal end 88 of battery housing 84. In the illustrated embodiment, two, inverted J-shaped clip bodies 92, 94 are utilized to provide a hanging system to hang pump system 20 on hanger bar 16 of medical stand 12. See FIG. 1A. One of the J-shaped clips opens in a direction opposite the other J-shaped clip.

Similar numerals designate similar items throughout the drawings.

FIGS. 3A and 3B diagrammatically illustrate partial, cross-sectional front views and side views of pump system 20. As shown in FIG. 3A, pump input port 54 receives fluid from the fluid supply. Nozzle housing 66 which is part of output port 56 is fluidly coupled to output hose 25. Hose 25 is adapted to fit snugly onto nozzle housing 66 and the hose carries the pressurized fluid to surgical site 26 (see FIG. 1A).

FIG. 3B diagrammatically shows pump system 20 and hanger clips 92, 94 being laterally spaced apart. FIG. 3B also shows operator actuable slide switch 82 which is moved in the direction of arrow 83 in order to turn the entire pump system ON. As described earlier, in the best mode of the present invention, pump system 20 is disposable. Once switch 82 is closed (by pulling out the slide), the pump must be used and then discarded.

Some important features of the present invention include pump system 20 capable of being hung on hanger arm 16 of medical stand 12; and the physical relationship between battery housing 84, motor 80 and pump housing 46 (which defines one of the major elements of the pump) by vertically aligning these three elements. With this hanger feature, automated pump 20 can hang at any convenient location near the source of fluid which is fluidly attached to pump system 20 at input port 54. Another feature is output port 56 (including nozzle 66) being disposed laterally with respect pump housing 46 and disposed above input port 54. One of the primary features of the invention is the use of a pressure sensitive switch near output port 56.

FIG. 3C shows a detailed, partial cross-sectional view of automated pump 20. Motor 80 is mounted securely within motor housing 54. Battery housing 84 is attached at the upper portion of motor housing 42 via collar 44. Pump housing 46 is mounted securely within external pump housing 40.

Figure 4:
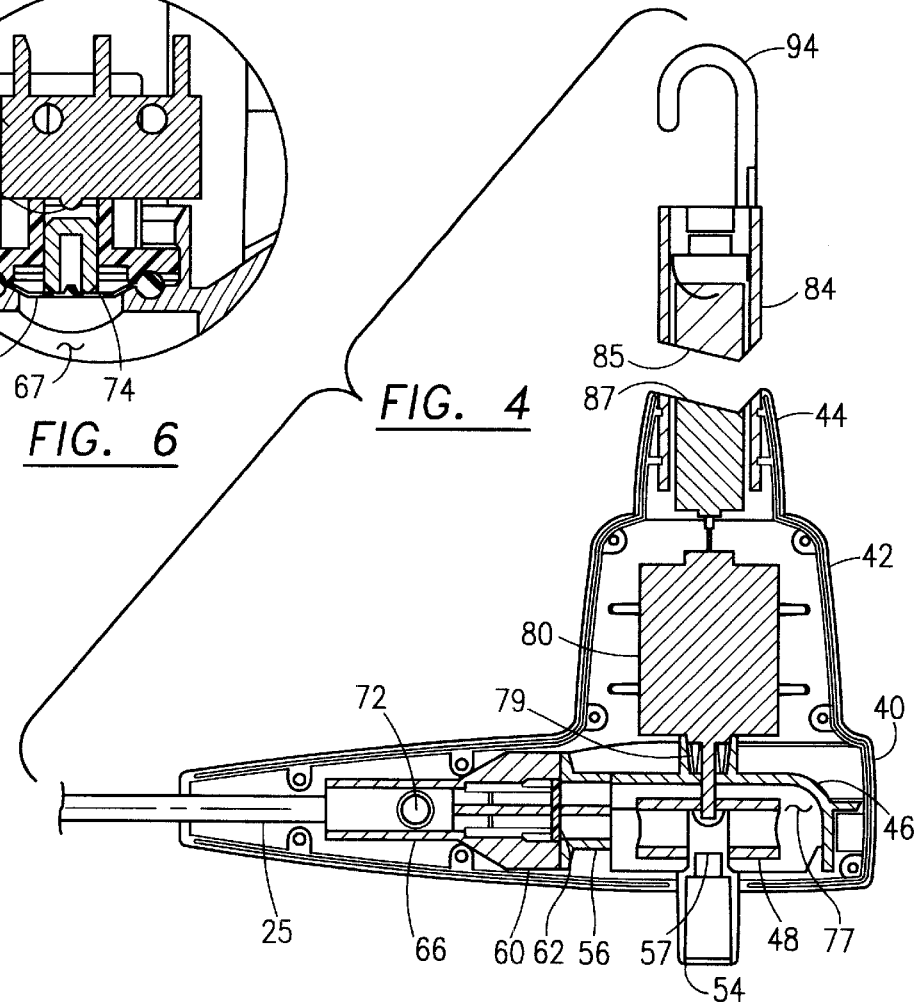
FIG. 4 diagrammatically illustrates a detailed, cross-sectional view of the pump system showing the lower portion of the battery housing, the motor, the pump impeller, the pump's input port and the pump's output port.

FIG. 4 diagrammatically illustrates a partial, cross-sectional view of the internal components of automated pump system 20. Battery housing 84 contains a plurality of batteries, two of which are batteries 85, 87. These batteries are currently AA sized. Impeller 48 is mechanically connected to motor 80 via a shaft with appropriate seals 79. Impeller 48 rotates within chamber 77. The rotation of impeller 48 draws fluid into input port 54. In the present embodiment, the pump is a centrifugal pump and impeller 48 rotates and draws fluid from input port 54 disposed beneath impeller 48. As impeller 48 rotates, the pressure in the fluid increases and the fluid is ejected through the check valve system which includes check valve disc 62 at output port 56. Fluid flow continues through check valve 62 and nozzle body 66. Pressure sensor diaphragm 72 senses the fluid pressure at a point immediately downstream check valve 62. Pressurized fluid is ejected through hose nozzle 66 to hose 25. To increase fluid flow, inboard end 57 of input port 54 is centrally located, on the axial centerline, and is positioned inboard of impeller 48. This inboard positioning increased flow about 0.25 l/min.

Figure 5:
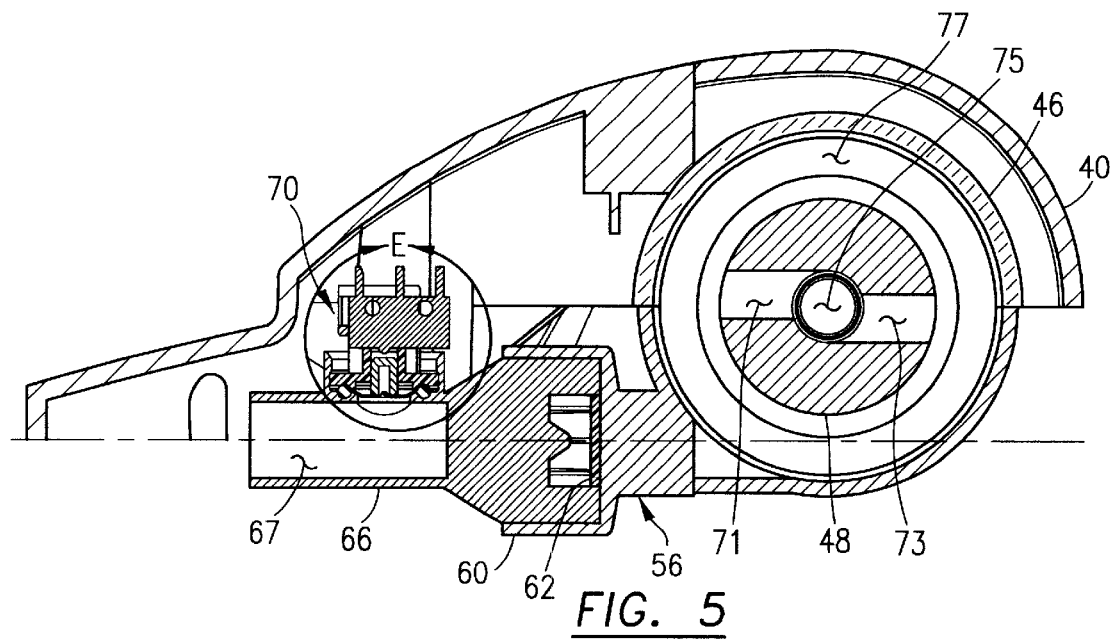
FIG. 5 diagrammatically illustrates a partial, cross-sectional view of the pump system impeller, output port and fluid pressure sensitive switch generally from the perspective of section line 5'–5" in FIG. 3A.

FIG. 5 shows a partial, cross-sectional, detailed view of the pump mechanism and its output port. Impeller 48 rotates and ejects fluid from internal passage 75 out through radial passages 71, 73. Fluid flow is ejected by impeller 48 into pump chamber 77. The resulting high pressure fluid exits pump output port 56 through check valve disc 62 and other common components of the check valve and through nozzle element 66. Fluid pressure sensitive switch 70 is immediately downstream of check valve 62 and either at or near pump output 56.

Figure 6:
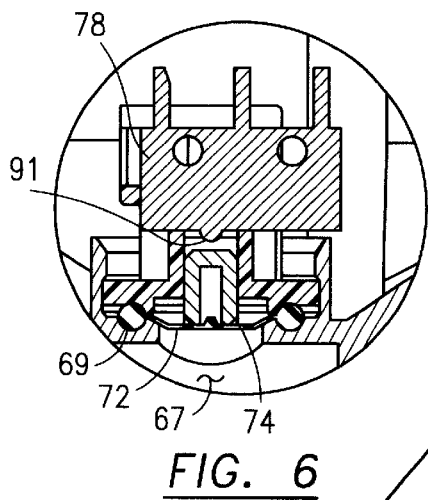
FIG. 6 diagrammatically illustrates the preferred embodiment of the pressure sensitive switch from detail area E in FIG. 5.

FIG. 6 shows a detailed view of fluid pressure sensitive switch 70 shown in detail area E in FIG. 5. Diaphragm 72 is sealed by seal 69 such that based upon fluid pressure in nozzle area 67, diaphragm 72 moves actuator pin or rod 74 towards or away from switch actuator 91. Switch actuator 91 operates to mechanically open or close the electrical switch in micro switch 78.

Although the present invention is shown utilizing various simple components such as a centrifugal pump and a micro switch activated by diaphragm, other pumps and switches can be utilized.

In operation, after the hydraulic system is connected and a fluid path is established from fluid source 18 through input line 23 to automatic pump 20, output line 25, manual valve control unit 30 (the system is "primed"), the operator pulls slide switch 82 (FIG. 2, FIG. 3B) and generally activates the automatic pump ON. Switch 78 is generally a normally closed switch. Since the pressure in output line 25 is less than the predetermined amount (herein approximately 5 psi), and since micro switch 78 is normally closed, the battery power is applied to motor M thereby turning ON the motor and driving impeller 48. Impeller 48 then pulls fluid into input port 54 and ejects fluid under pressure to output line 25. When the pressure in output line 25 exceeds a predetermined value established by diaphragm 72 and any biasing mechanism (e.g. spring or tension fit of the diaphragm), actuator pin 74 depresses actuator lever 91 and switch 78 opens the electrical circuit and turns the motor OFF. When the pressure falls below the predetermined value in output line 25, diaphragm 72 senses and reacts to the pressure and moves actuator 74 outboard away from mechanical actuator 91 and turns switch 78 to its normally closed ON position thereby reestablishing an electrical circuit between the batteries and motor 80. Preferably, diaphragm 72 is made of silicone. Various types of biasing mechanism such as springs or a tension established on diaphragm 72 may be utilized. Other types of pressure sensors may be utilized, for example, digital pressure sensors. These sensors may require digital circuitry.

Although the currently proposed system has the pressure sensitive switch near output port 56, the system will work if the pressure sensitive switch is fluidly coupled anywhere between the pump output and valving unit 30.

The claims appended hereto are meant to cover modifications and changes within the scope and spirit of the present invention.

What is claimed is:

1. An automatically controlled pump for supplying pressurized fluid via an output line to a surgical site, said pump adapted to be coupled to a fluid source via an input line, said pump comprising:

a motor and a motor housing;

a pump disposed within a pump housing, said pump having a rotatably disposed impeller coupled to said motor, said pump housing defining a fluid input and a fluid output port respectively adapted to be coupled to said input and said output line;

said motor powered by at least one battery;

a switch, turning ON and OFF said motor and controlled by fluid pressure at or near said fluid output port; and, said pump housing attached below said motor housing wherein said motor is powered by at least one battery mounted in a battery housing above said pump housing.

2. A pump as claimed in claim 1 wherein said input port is disposed beneath said pump housing.

3. A pump as claimed in claim 2 wherein said output port is disposed substantially laterally with respect to said pump housing.

4. A pump as claimed in claim 3 including a manual ON and OFF switch for said motor.

5. A pump as claimed in claim 4 including a check valve mounted in said pump housing upstream of said fluid pressure controlled switch.

6. A pump as claimed in claim 5 wherein said input port has an inboard end which is disposed inboard of said impeller.

7. A pump as claimed in claim 1 wherein said input port has an inboard end which is disposed inboard of said impeller.

8. A method of automatically controlling a pump and supplying pressurized fluid via an output line to a surgical site, said pump adapted to be coupled to a fluid source, the method comprising the steps of:

providing a battery powered motor mechanically coupled to said pump;

monitoring fluid pressure with respect to the pump's output and turning ON and OFF said motor based upon fluid pressure above or below a predetermined value in said output line coupled thereto; and supplying fluid from said fluid source beneath said pump's output; and supplying battery power to said motor above said pump's output.

9. A method of controlling a pump as claimed in claim 8 wherein said step of monitoring and turning ON and OFF occurs without operator intervention.

10. A method of controlling a pump as claimed in claim 9 including the step of manually removing battery power from said motor with operator intervention.

11. A method of controlling a pump as claimed in claim 8 including permitting substantially one way fluid flow from said pump's output and wherein the step of monitoring occurs downstream of said one way fluid flow.

12. An automatically controlled pump for supplying pressurized fluid via an output line to a surgical site, said pump adapted to be coupled to a fluid source via an input line, said pump comprising:

a motor and a motor housing;

a pump disposed within a pump housing, said pump having a rotatably disposed impeller coupled to said motor, said pump housing defining a fluid input and a fluid output port respectively adapted to be coupled to said input and said output line;

said motor powered by at least one battery;

a switch, turning ON and OFF said motor and controlled by fluid pressure at or near said fluid output port; and, said pump housing attached below said motor housing wherein said battery housing forms a hanger on a terminal end remote from said pump housing.

13. A pump as claimed in claim 12 wherein said input port is disposed beneath said pump housing.

14. A pump as claimed in claim 13 wherein said output port is disposed substantially laterally with respect to said pump housing.

15. A pump as claimed in claim 14 including a manual ON and OFF switch for said motor.

16. A pump as claimed in claim 15 including a check value mounted in said pump housing upstream of said fluid pressure controlled switch.

17. A pump as claimed in claim 16 wherein said input port has an inboard end which is disposed inboard of said impeller.

18. A pump as claimed in claim 12 wherein said input port has an inboard end which is disposed inboard of said impeller.

* * * * *